United States Patent [19]

Hu

[11] Patent Number: 5,377,250
[45] Date of Patent: Dec. 27, 1994

[54] RECONSTRUCTION METHOD FOR HELICAL SCANNING COMPUTED TOMOGRAPHY APPARATUS WITH MULTI-ROW DETECTOR ARRAY

[75] Inventor: Hui Hu, Waukesha, Wis.

[73] Assignee: General Electric Company, Milwaukee, Wis.

[21] Appl. No.: 945,758

[22] Filed: Sep. 16, 1992

Related U.S. Application Data

[63] Continuation-in-part of Ser. No. 926,987, Aug. 7, 1992, Pat. No. 5,291,402.

[51] Int. Cl.⁵ .................... G01N 23/04; G01N 23/083
[52] U.S. Cl. ................................ 378/15; 378/14; 378/901; 364/413.15
[58] Field of Search ............... 378/4, 14, 15, 901; 364/413.14, 413.15

[56] References Cited

U.S. PATENT DOCUMENTS 5,170,439 12/1992 Zeng et al. .......................... 382/6
5,270,926 12/1993 Tam ............................. 364/413.19
5,291,402 3/1994 Pfoh .............................. 364/413.14

OTHER PUBLICATIONS

Practical Cone–Beam Algorithm, Feldkamp et al., J. Opt. Soc. Am. A/vol. 1, No. 6/Jun. 1984.

*Primary Examiner*—Paul M. Dzierzynski
*Assistant Examiner*—David V. Bruce
*Attorney, Agent, or Firm*—Quarles & Brady

[57] ABSTRACT

An x-ray computed tomography system for helically scanning a patient, by translating the patient as projections of the patient at various beam angles are obtained, employs a detector array having multiple rows displaced in along the direction of translation. The voxel attenuation values reconstructed from the multiple rows are combined to produce an image having an improved beam profile in along the translation direction. A cone beam reconstruction method, which accounts for the divergence of the rays of a fan beam of x-rays, and helical scanning is used to further improve the slice profile. The voxels may be selected so that they cluster closely about the position of the desired slice plane.

14 Claims, 7 Drawing Sheets

RECONSTRUCTION METHOD FOR HELICAL SCANNING COMPUTED TOMOGRAPHY APPARATUS WITH MULTI-ROW DETECTOR ARRAY

This application is a continuation-in-part of U.S. application Ser. No. 07/926,987 filed Aug. 7, 1992 now U.S. Pat. No. 5,291,402, and entitled: HELICAL SCANNING COMPUTED TOMOGRAPHY APPARATUS WITH MULTI-ROW DETECTOR ARRAY.

BACKGROUND OF THE INVENTION

This invention relates to computed tomography ("CT") systems where the patient is moved continuously during the scanning and more specifically to a CT apparatus employing multiple rows of detector elements displaced along the axis of patient movement.

Fan Beam Computed Tomography

Referring to FIG. 1, in a prior art fan beam x-ray computed tomography system, an x-ray source 10 is collimated to form a generally planar fan beam 12, along a beam axis 13. The fan beam is orientated to lie within the x-y plane of a Cartesian coordinate system, termed the "imaging plane", and diverges about the beam axis 13 within the imaging plane with a defined fan beam angle $\gamma$.

The fan beam 12 projects through an imaged object 14 to an x-ray detector array 16 also lying within the imaging plane. The detector array 16 is comprised of a large number of adjacent detector elements 18 which each measure the intensity of transmitted radiation along a different ray extending between the x-ray source 10 and that particular detector element 18. The detector elements 18 can be organized along an arc each to intercept x-rays from the x-ray source 10 along a different ray of the fan beam 12.

The x-ray source 10 and detector array 16 may be rotated on a gantry 20 within the imaging plane, around an axis of rotation 15, ordinarily within the imaged object 14, so that the fan beam 12 intercepts the imaged object 14 at different gantry angles $\beta$. At a number of gantry angles $\beta$, spaced by a gantry angle increment, projections are acquired, each comprised of the intensity signals from each of the detector elements 18. The intensity signals are a function of the attenuation of the fan beam 12 along each ray by the imaged object 14 and hence of the density of the elements of the imaged object 14 along the path of the ray. The gantry 20 is then rotated to a new angle $\beta$ and the process is repeated to collect a number of projections at different angles $\beta$ to form a tomographic projection set.

The acquired tomographic projection set is typically stored in numerical form for computer processing to "reconstruct" a slice image according to reconstruction techniques known in the art such as "filtered backprojection". The reconstructed slice images may be displayed on a conventional CRT tube (not shown) or may be converted to a film record by means of a computer controlled camera (not shown).

A typical computed tomographic study entails the imaging of a series of slices of the imaged object 14 at slice planes parallel to the imaging plane. Each slice is displaced incrementally along a z-axis perpendicular to the x- and y-axes, so as to provide a third spatial dimension of information. A user may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, narrower fan beams 12 and detector arrays 16 are employed and additional slices may be taken in the z-dimension. The time and expense of a tomographic study increases with the number of slices required. Longer scan times increase the discomfort to the patient, who must remain nearly motionless to preserve the fidelity of the tomographic reconstructions, and increase the chance of image artifacts caused by voluntary or involuntary movement. There is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

Helical CT Scanning

A reduction in patient repositioning time may be accomplished by translating the patient in the z-axis synchronously with the rotation of the gantry. Referring still to FIG. 1, the combination of constant patient translation along the z-axis during the rotation of the gantry 20 and acquisition of projection data, has been termed "helical scanning" and refers to the apparent helical path 22 of the beam axis 13 with respect to the imaged object 14. The "pitch" of the helix, being the z-axis distance traversed by the imaged object 14 for one complete revolution of the gantry, is generally set equal to the width of the slices of which images will be reconstructed, and is generally related to the width of the fan beam 12 and detector array 16 along the z-axis. As used herein, "helical scanning" shall refer generally to the use of continuous translation of the patient or imaged object during the acquisition of tomographic imaging data, as opposed to "stop and shoot" scanning which will refer to the acquisition of the tomographic data set without translation of the patient or imaged object during the acquisition of a projection set.

Continuous translation of the imaged object during scanning shortens the total scanning time required, for the acquisition of a given number of slices, by eliminating the length of time nominally required for repositioning the patient between scans. Unfortunately, helical scanning may also introduce certain errors in the data of the acquired tomographic projection sets.

The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object along the z-axis. The severity of the image artifacts depends generally on the "helix offset" in the projection data, measured as the difference between the table locations of the scanned data and the z-axis value of the desired slice plane. Errors resulting from helical scanning will be referred to collectively as "skew" errors.

Several methods have been used to reduce skew errors in helical scanning. A first approach disclosed in U.S. Pat. No. 5,046,003, issued Sep. 3, 1991, entitled "Method for Reducing Skew Image Artifacts in Helical Projection Scanning", assigned to the same assignee as the present invention, and hereby incorporated by reference, uses non-uniform table motion to concentrate the helically acquired projections near the slice plane while limiting the accelerative forces on the patient. One disadvantage to this approach is that the slice planes must be determined before the scanning takes place.

A second approach, typified by co-pending U.S. patent application Ser. No. 07/430,372, filed Nov. 2, 1989, now U.S. Pat. No. 5,270,923, entitled: "Computerized Tomographic Image Reconstruction Method for Helical Scanning", and Ser. No. 07/435,980, filed Nov. 13, 1989 now U.S. Pat. No. 5,233,518, entitled: "Extrapolative Reconstruction Method for Helical Scanning", assigned to the same assignee as the present invention, and incorporated by reference, skew artifacts are reduced by interpolating and/or extrapolating between the data of projection sets acquired at different gantry angles and hence at different z-axis positions with respect to the imaged object 14. The interpolation process provides effective projection data at a fixed slice plane and over a range of gantry angles $\beta$ despite the fact that each projection is in fact acquired at a different slice plane for each of the gantry angles $\beta$ because of the helical scanning.

A drawback to interpolation and extrapolation in correcting helically scanned data is that these processes reduce the resolution of the acquired projection data along the z-axis by increasing the effective beam profile along the z-axis. The spatial resolution of a CT system is a measure of the smallest object that may be resolved by the CT system; all other conditions being equal, higher resolution (the ability to image smaller objects) is preferred.

The resolution of the projection data along the z-axis is determined principally by the geometry of the fan beam 12 and detector array 16. Referring to FIG. 2(a), in a prior art system, a focal spot 26 from which the fan beam 12 emanates and within the x-ray source 10, will have a finite z-axis extent, generally, on the order of one millimeter or more. X-rays emanate from the focal spot 26 at a relatively wide range of angles and are collimated by x-ray opaque blades of collimator 24. The blades of collimator 24 together form a slot generating the desired width of the fan beam 12 in the z-axis direction.

Even with the collimation by collimator 24, the fan beam 12 will typically diverge with respect to the z-axis before striking the face of a given detector element 18. The z-axis extent of the focal spot 26 is finite and the blades of the collimator 24 are necessarily displaced from the detector element 18, therefore, the effective width of the fan beam 12 along the z-axis, and hence the z-axis resolution of the system, will thus vary somewhat depending on how far one moves from the focal spot 26 toward the detector element 18.

The width of fan beam 12 may be characterized by its intensity profile 28 which plots x-ray intensity versus z-axis position as measured the axis of rotation. The intensity of the fan beam shown by profile 28, drops off at its z-axis extremes as a result of a "penumbra effect" caused by the finite axis extent of the focal spot 26. Specifically, points within the fan beam 12 in a penumbra 17 at either z-axis extreme of the fan beam 12 are illuminated by less than the full area of the focal spot 26 as a result of progressive shadowing of the blades of the collimator 24. As a result of the penumbra effect, the intensity profile 28 of the radiation will be generally trapezoidal with the intensity falling linearly at either z-axis extreme. This tailing off of intensity at the edges of the fan beam 12 is undesirable to the extent that it increases the width of the intensity profile 28. For increasingly narrow fan beams 12 the penumbra effect becomes more significant and as a practical matter, therefore, the penumbra effect limits the minimum z-axis width of the fan beam 12 and hence the z-axis resolution of the CT system.

At the surface of the detector elements 18, the fan beam 12 and the penumbra 17 widen to produce an intensity profile 28' similar to intensity profile but stretched along the z-axis to substantially span the z-axis width of the detector elements 18.

Referring to FIG. 2(b), a slice profile 30 plots the signal developed by each detector element 18 as a function of z-axis position along the face of the element 18. The slice profile 30 will be a function of the intensity profile 28 and a function indicating the sensitivity of the detector element 18 with z-axis position. Generally the sensitivity of the detector element 18 also falls off at its z-axis limits so that values of the slice profile 30 drop rapidly for positions in the penumbra 17 which are also near the edge of the detector element 18. The z-axis resolution of the scanning system will generally be considered to be the width of this slice profile 30 at half of its maximum value (Full Width Half Maximum or FWHM) designated "s".

Referring now to FIG. 2(c), in the helical scanning described above, the beam axis 13 of the fan beam 12 will progress along the z-axis with respect to the imaged object 14 as the beam axis 13 rotates through different gantry angles $\beta$ as shogun by trajectory 32. The interpolation of projection data acquired in a helical scan recognizes the general equivalence of projections taken at different z positions but at gantry angles $\beta$ differing by 360° or $2\pi$ radians. Accordingly, after every $2\pi$ (or 360°) of gantry angles $\beta$ the trajectory is mapped to angles $\beta$ between 0 and $2\pi$, however the gantry angles $\beta$ should be understood to in fact increase monotonically with the trajectory 32 being a continuous straight line. Ordinarily the pitch of the helical scan, being the amount of z-axis translation for each 360° of gantry rotation, is set equal to this FWHM of slice profile 30: s.

An interpolated projection set at a slice plane $Z_r$, having projection data for a full range of gantry angles from 0 to $2\pi$ is obtained by selecting projection data at points P and Q at gantry angles differing by $2\pi$ and at z positions on either side of the slice plane $Z_r$. Data for the point R in the slice plane $Z_r$ may then be interpolated from the data at points P and Q. The interpolation is performed by weighting the data of each projection P and Q by a weighting factor which is a function on the distance between the slice plane $Z_r$ and the z-axis positions of each of points P and Q and summing the weighted projection data at points P and Q together. Specifically, for a given gantry angle $\beta$ and a slice plane $Z_r$, the value of the projection at R in the slice plane $Z_r$ is:

$$R(Z_r, \beta) = w(\Delta Z_p)P(Z_p, \beta) + w(\Delta Z_q)Q(Z_q, \beta) \quad (1)$$

where $\Delta Z_p$ and $\Delta Z_q$ are the differences along the z-axis between the slice plane $Z_r$ and points P and Q respectively and w is the weighting function 33 shown in FIG. 2(d) which varies linearly between zero and one for magnitudes of $\Delta Z_p$ and $\Delta Z_q$ between s and zero. The weighting function is generally triangular and linearly decreases the weight of a given projection with increasing distance from the slice plane. An entire projection set may be constructed for the slice plane $Z_r$ by using additional flanking points for other values of $\beta$.

The effect of the weighting function 33 is to produce an interpolated slice profile 34 substantially wider (with greater FWHM) than the slice profile 30. This results from the fact that the interpolated slice profile 34 will include data from slice profiles 30 taken over a z-axis range of 2 s. This larger interpolated slice profile, intrinsic to the interpolation required to reduce skew errors in helical scanning, detrimentally affects the z-axis resolution of the acquired projection data.

SUMMARY OF THE INVENTION

The parent application to this continuation-in-part describes an apparatus for improving the effective beam profile or FWHM by combining the signals from rows of a subdivided detector having multiple narrow rows of detector elements. This method will be described in detail further below.

The present invention has recognized that the edgemost rows of detectors receive fan beam rays at an angle deviating from the slice plane. This deviation degrades the slice profile or FWHM when the data of the projections are combined and then reconstructed using conventional fan beam reconstruction methods. Accordingly, the present invention combines data after reconstruction by a "cone beam" reconstruction technique which more accurately accounts for the angular deviation of the fan beam and thereby prevents degradation of the slice profile by the data of the edge rows. Cone beam reconstruction techniques are generally known in the art for use in simultaneously acquiring multiple projections, but not for improving slice profile of a single slice.

Specifically, in the present method, an x-ray beam is generated along a beam axis, the beam including a plurality of rays along paths diverging conically from a focal spot and spaced in two dimensions with respect to the beam axis first along a translation axis in columns and second along a transverse axis perpendicular to the translation axis in rows. The beam axis is moved throughout a plurality of beam angles about the translation axis and the rays are received by a detector, after passing through the imaged object at the plurality of beam angles, the detector producing an intensity signal associated with each ray. The intensity signals for the rows of rays form a plurality of one dimensional row projections of a projection set. During the movement of the beam axis throughout the plurality of beam angles to obtain a projection set of row projections, the imaged object is translated along the translation axis with respect to the x-ray source.

The acquired row projections of the projection set are first filtered according to the spatial frequencies of the row projections and then backprojected along the path of each ray associated with each intensity signal of the row projections to produce voxels of data.

After a slice plane has been identified, selected voxels near the slice plane are combined into an image slice and the image slice is displayed.

It is one object of the invention to reduce the effect, on beam profile, of the divergence of the x-ray beam along the translation axis and away from the beam axis. By backprojecting along the actual ray paths rather than assuming each ray path is perpendicular to the translation axis (i.e., has no z-axis divergence) the accuracy of the backprojected voxels is improved. The combination of these more accurate voxels in the image domain, rather than the combination of raw intensity signal prior to backprojection, improves the beam profile and hence the resolution of the image along the translation axis.

The beam angles of subsequent row projections are separated by an angular spacing and the step of backprojecting each ray of the projection set along its path backprojects only those rays from row projections having beam angles in a range of not more than $2\pi$ minus the angular spacing.

This limitation in angular range is employed because it has been recognized that the diverging rays of the fan beam at the detector edges, unlike truly parallel rays, overlap with the diverging rays from previous and later fan beams causing data to be measured twice. In the present invention, each slice is reconstructed from data only over $2\pi$ radians, centered about the slice, to eliminate redundancy and avoid possible image artifacts.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 3:
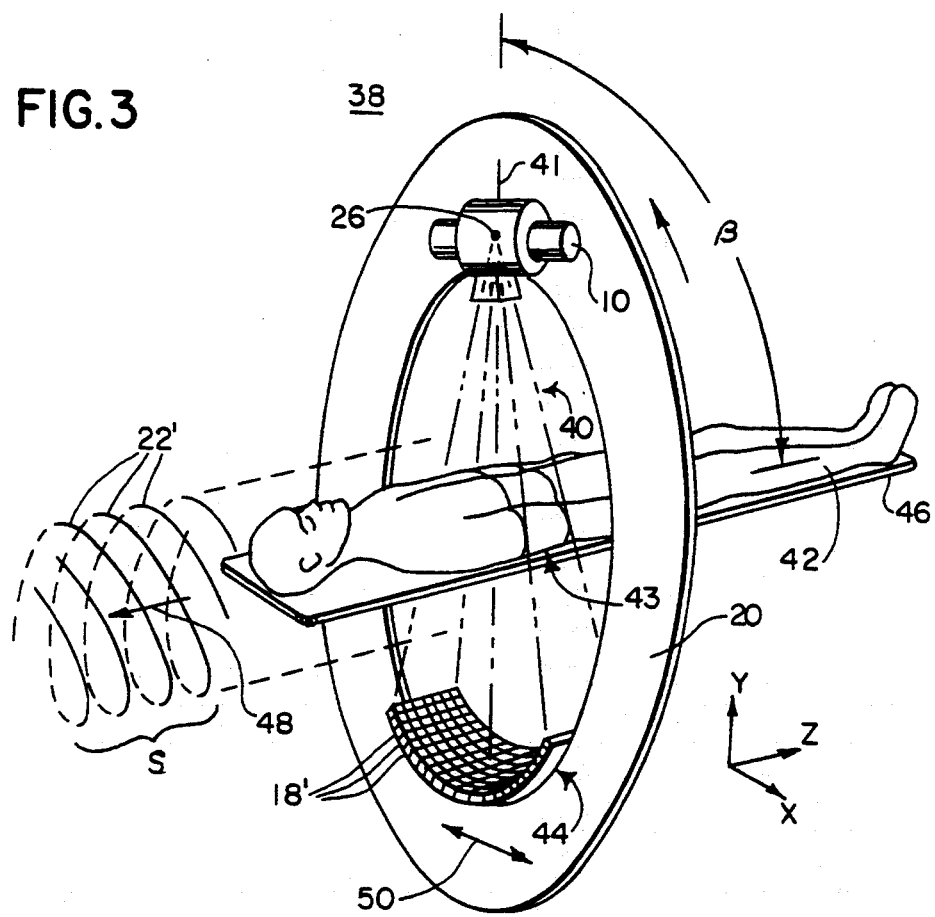
FIG. 3 is a pictorial representation of the CT apparatus of the present invention including a detector array having rows and columns of detector elements and a fan beam.

Referring to FIG. 3, a CT scanner for use with the present invention includes a gantry 20 supporting an x-ray source 10 oriented to project a fan beam 40 of x-rays along a beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by angle β from an arbitrary reference position within the gantry plane 38.

The patient 42 rests on a table 46 that may be moved along a translation axis 48 aligned with the z-axis of the Cartesian coordinate system. The table 46 crosses the gantry plane 38 and is radiotranslucent so as not to interfere with the imaging process.

The x-rays of the fan beam 40 diverge from the beam axis 41 and the gantry plane 38, along the translation axis 48, and also diverge from the beam axis 41 along the gantry plane 38 and along a transverse axis 50 generally orthogonal to both the beam axis 41 and the translation axis 48.

Figure 1:
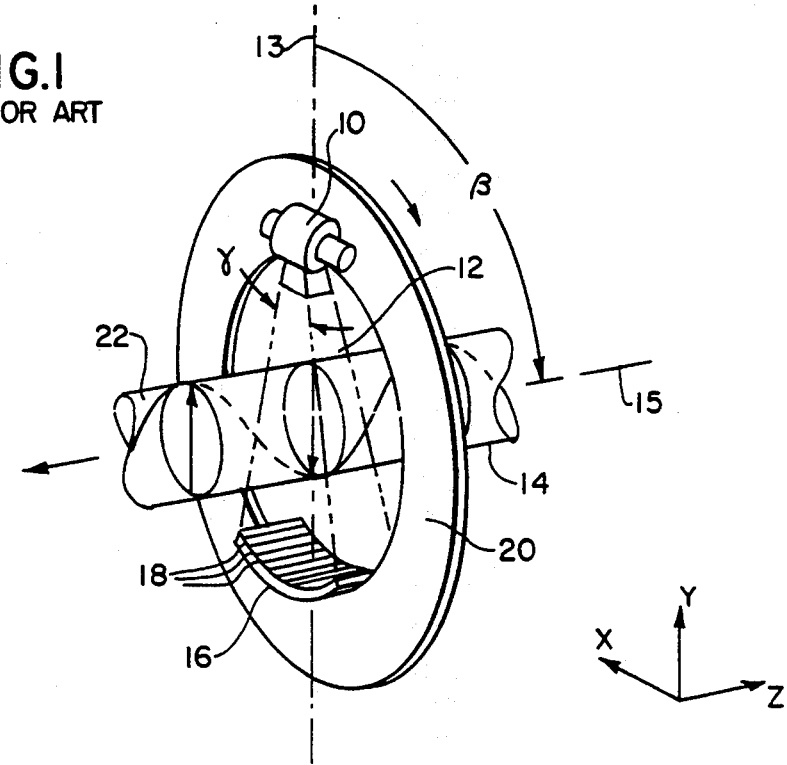
FIG. 1 is a pictorial representation of a prior art CT gantry and imaged object showing the helical scanning of a fan beam and the relative angles and axes associated therewith as discussed in the Background of the Invention above.

After passing through the patient 42, the x-rays of the fan beam 40 are received by the detector array 44, which unlike the detector array 16 of FIG. 1, has multiple rows of detector elements 18'. The detector elements 18' arranged in rows along the transverse axis 50 and columns along the translation axis 48. The surface of the detector array 44 may be planar or may describe a section of the surface of a sphere or cylinder having a center at the focal spot 26.

The detector elements 18' each receive x-rays and provide intensity measurements along separate rays of the fan beam 40. The intensity measurements together describe the attenuation of the fan beam 40 by a volume 43 of the patient 42 hence the average density of that volume 43 of the patient 42.

In the preferred embodiment, this volume is substantially equal to the slice volume measured by a conventional fan beam CT system, and the width of the detector array 44, as measured along its columns, is approximately equal to the width of a similar detector for a conventional stop and shoot fan beam system. Accordingly, the columns of detector elements 18' simply subdivide a conventional fan beam detector array 16, such as shown in FIG. 1, along the z-axis.

Figure 4:
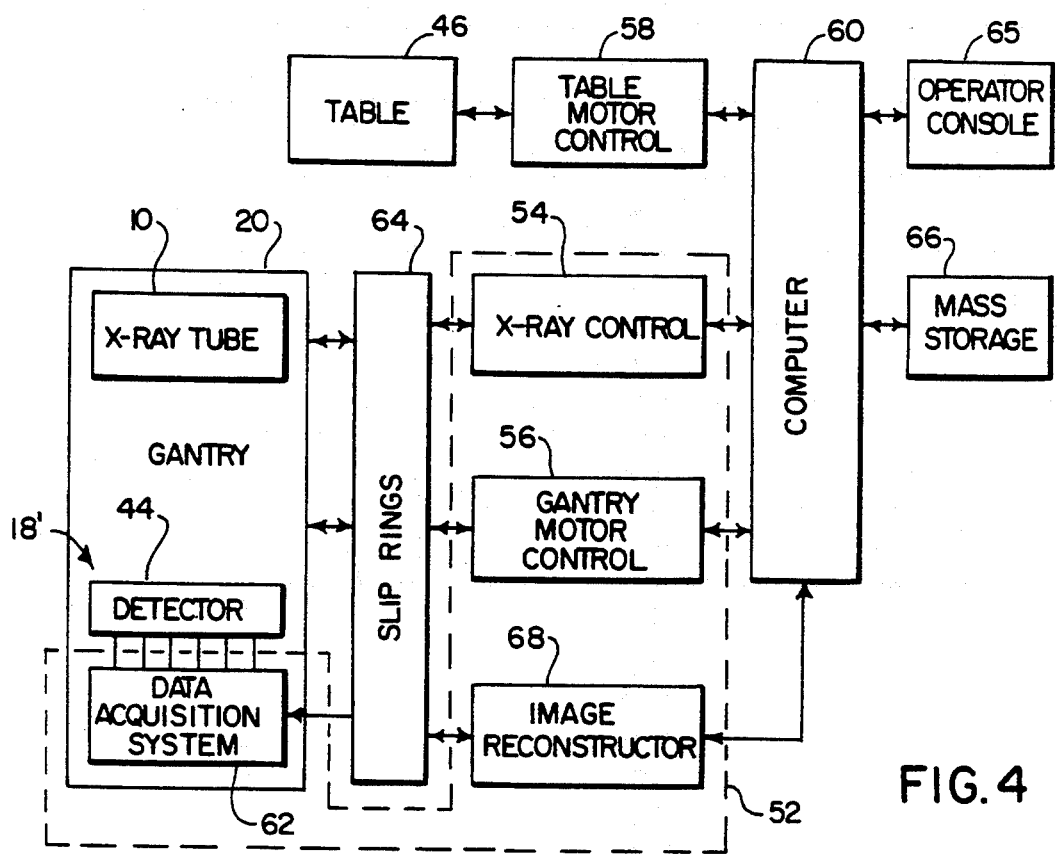
FIG. 4 is a block diagram of a CT control system that may be used with the CT apparatus of FIG. 3 and that is useful for practicing the present invention.

Referring now to FIG. 4, the control system of a CT imaging system of FIG. 3, has gantry associated control modules 52 which include an x-ray control 54, a gantry motor control 56, a data acquisition system 62 and an image reconstructor 68. The x-ray control 54 provides power and timing signals to the x-ray source 10 to turn it on and off as required under the control of a computer 60. The gantry motor control 56 controls the rotational speed and position of the gantry 20 and provides information to the computer 60 regarding gantry position. The data acquisition system 62 samples and digitizes intensity signals from the detector elements 18 of detector array 44, and the image reconstructor 68 receives the sampled and digitized intensity signals from the data acquisition system 62, each identified as to row and column of the detector element of the detector array 44, and combines the intensity signals from the detector elements 18 according to the present invention, and performs high speed image reconstruction according to methods known in the art.

Each of the above modules is connected to its associated elements on the gantry 20 via slip rings 64 and serves to interface computer 60 to various gantry functions. The slip rings 64 permit the gantry 20 to rotate continuously through angles greater than 360° to acquire projection data.

The speed and position of table 46 along the translation axis 48 is communicated to and controlled by computer 60 by means of table motor control 58. The computer 60 receives con, hands and scanning parameters via operator console 65 which is generally a CRT display and keyboard which allows an operator to enter parameters for the scan and to display the reconstructed image and other information from the computer 60. A mass storage device 66 provides a means for storing operating programs for the CT imaging system, as well as image data for future reference by the operator. Both the computer 60 and the image reconstructor have associated electronic memory (not shown) for storing data.

In operation, the gantry motor control 56 brings the gantry 20 up to rotational speed and the table motor control begins translation of the table 46. The x-ray control 54 turns on the x-ray source 10 and projection data is acquired on a continuous basis. At each gantry angle $\beta$, the projection acquired comprises of intensity signals identified to each detector element 18' at each particular row and column of the detector array 44.

Figure 2A:
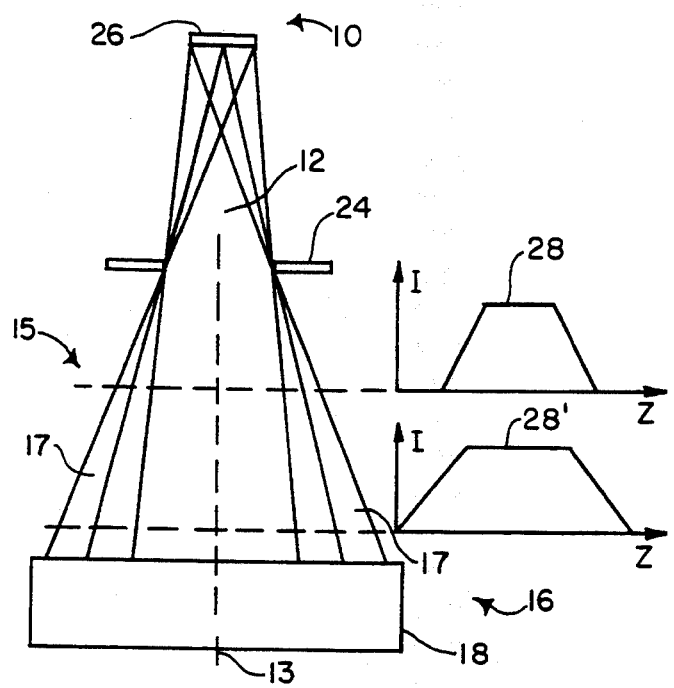
FIG. 2(a) is an exaggerated cross-section of the fan beam of FIG. 1 showing penumbra caused by a collimator.
Figure 5:
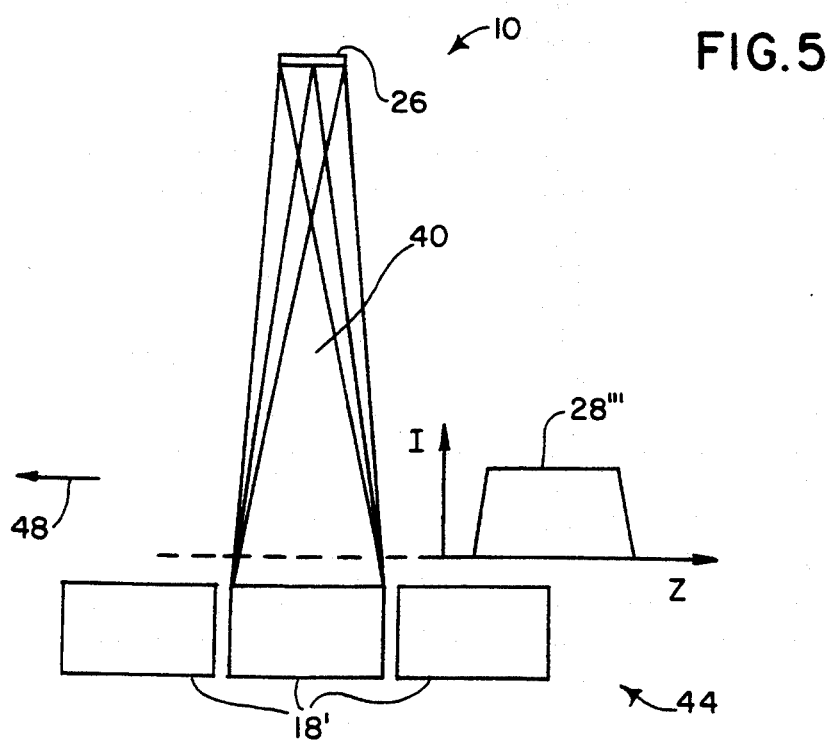
FIG. 5 is an exaggerated cross-section of a portion of the detector array of FIG. 3 and a portion of the fan beam showing the reduction of penumbra.

Referring now to FIG. 5, the use of multiple detector elements in columns along the z-axis, or translation axis, substantially eliminates the penumbra 17 incident to the use of the blades of collimator 24 shown in FIG. 2(a). Each detector element 18' of a column is electrically independent and thus all but the detector elements 18' at the z-axis extremes of the columns are self-collimating insofar as the physical extent of each detector element 18' serves to define the rays 79 of the fan beam 40 to which it is sensitive rather than a separate collimator. The face of the detector elements 18, for all but the elements 18 at the extreme ends of the column, are unobstructed by a collimator to be fully illuminated by the entire area of the focal spot 26 eliminating any penumbra 17. This "self collimation" substantially sharpens the rectangular intensity profile 28''' seen by each detector element 18. The lack of a penumbra 17 is instrumental in allowing multiple detector elements 18 in each row of the detector array 44 without unduly reducing the practical working area of the detector array.

Figure 2B:
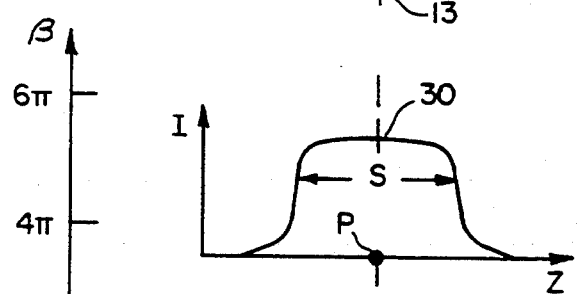
FIG. 2(b) is a graphical representation of the slice profile produced by the fan beam of FIG. 2(a)
Figure 2C:
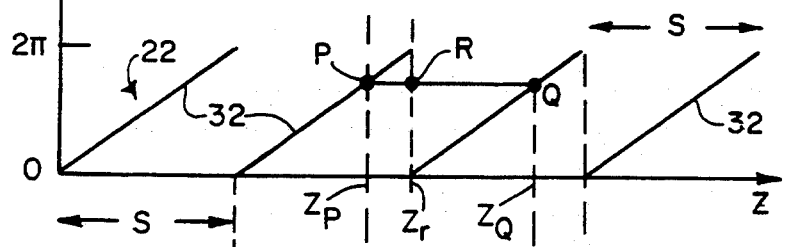
FIG. 2(c) is a graphical representation of the trajectory of the center of the fan beam of FIG. 2(a), with helical scanning, along the z-dimension with increasing gantry angle β.
Figure 2D:
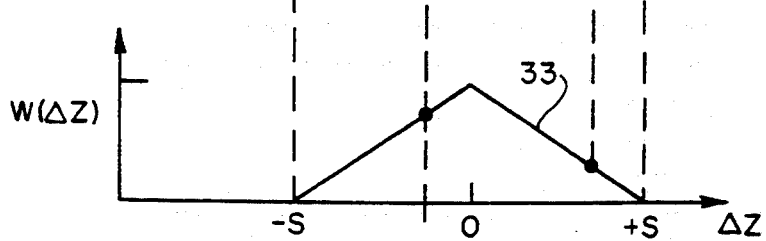
FIG. 2(d) is a graphical representation of a weighting function used for interpolation to reduce the effects of skew error in the helical scanning of FIG. 2(c)
Figure 2E:
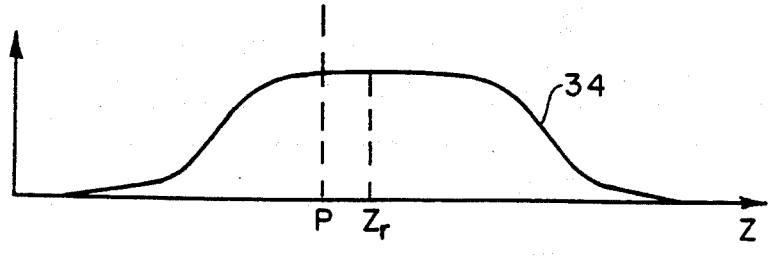
FIG. 2(e) is a graphical representation similar to FIG. 2(b) showing the effective slice profile of the fan beam of FIG. 1 after interpolation with the weighting function of FIG. 2(d)

Referring now to FIGS. 6(a)–(d), the intensity profile 28''' is substantially narrower than the intensity profile 28' shogun in FIG. 2(a) as a result of the breaking of the detector array 44 into columns of multiple detector elements 18. The intensity profile 28''' corresponds to a slice profile 30' shown in FIG. 6(b) having an FWHM of s' which, in the preferred embodiment, is significantly less than FWHM s shown in FIG. 2(b) the latter being equal to the slice width of the CT system.

Figure 6A:
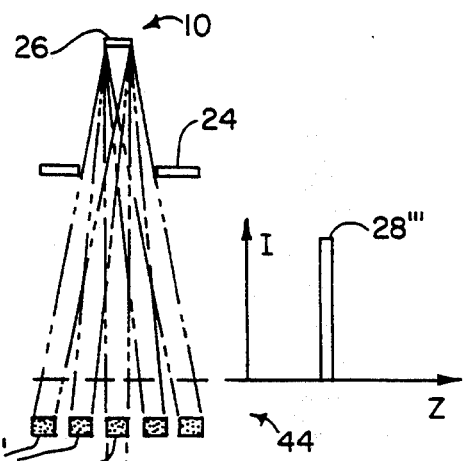
FIG. 6(a) is a cross-section of the entire fan beam and detector array of FIG. 5.
Figure 6B:
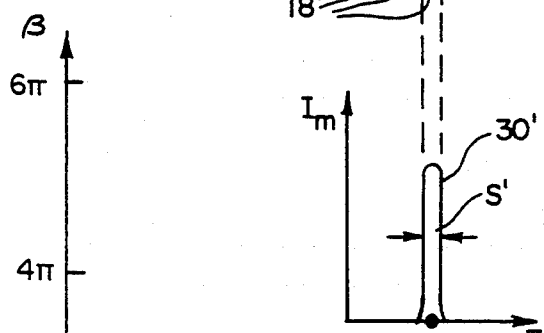
FIG. 6(b) is a graphical representation of the slice profile produced by the fan beam of FIG. 5(a) and a single detector element.
Figure 6C:
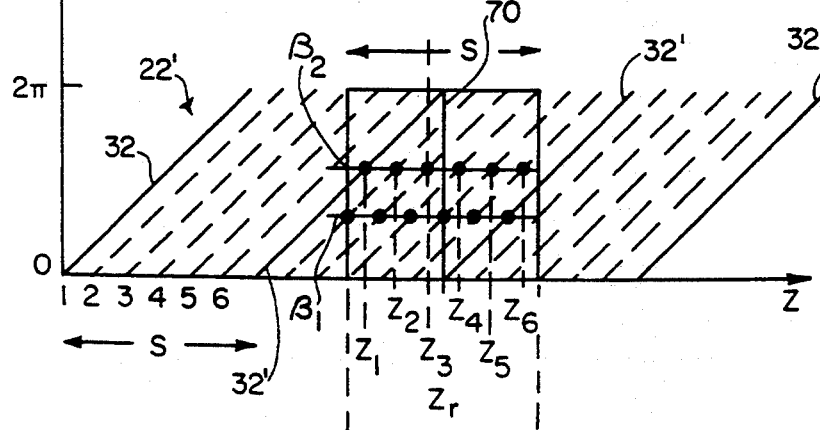
FIG. 6(c) is a graphical representation of the trajectory of each ray associated with a single detector element of FIG. 6(a), with helical scanning, along the z-dimension with increasing gantry angle β.

Referring now to FIGS. 3 and 6(c), the CT system of the present invention maintains the helical pitch of s employed by the systems of FIG. 1, that is, for each full revolution of the gantry 20, the patient 42 is translated by an amount equal to a slice thickness s as shown by trajectory 32', however, it will be recognized that translation amounts different than s may also be used. At each angle $\beta$ of the gantry 20, however, multiple intensity signals are obtained along the z-axis from each detector element 18' within a column of the detector array 44. Thus, whereas in a conventional CT system at each gantry angle $\beta$, a projection is acquired associated with a single point along the z-axis; in the present invention multiple thin projections are acquired associated with multiple contiguous points along the z-axis.

Referring to FIGS. 3 and 6(c), each detector element 18' within a column of the detector array 44 traces its own helix 22' having a pitch s essentially identical to the pitch of a conventional CT machine but interleaved with the helices 22' of the other detector elements 18 within that column. Thus, the spacing along the z-axis between the points at which projection data is acquired by adjacent detector elements 18 within a column is substantially less than s, i.e., less than the spacing along the z-axis between the points at which projection data is acquired by detector elements 18 in consecutive scans of a conventional CT system.

Accordingly, the interpolation of a projection set for an arbitrary slice at position $Z_r$ may employ as few as two points separated by as little as s' rather than s. As a result, the expansion of the effective beam profile caused by the interpolation to a slice plane at $Z_r$ is much reduced.

Although, in principle, only two points at z-axis positions straddling the slice plane $Z_r$ are required to interpolate an intensity value at the slice plane $Z_r$, in the present embodiment, for reasons of providing adequate signal-to-noise ratio, multiple points are used to generate a composite signal and interpolation, as such, is not used. Further, the composite signal is not generated by combining the intensity signals directly, but rather the intensity signals are reconstructed into an image and volume elements of the image (voxels) are combined to generate a composite signal which is the ultimate image to be obtained. This reconstruction process will be described in detail below.

The voxels used for the reconstruction are those clustered around the slice plane $Z_r$ and the intensity signals from which those voxels are reconstructed will be selected from projections associated with the multiple rows of the detector array 44 at a given gantry angle $\beta$ having intensity signals associated with proximate positions to $Z_r$ and for the projections associated with detector rows at other gantry angles $\beta$ preceding or following the given gantry angle. For a detector array 44 having six rows and hence six detector elements 18' in each column, for example, the voxels to be combined will be derived from six intensity signals which are selected from those projections clustered symmetrically on each side of the desired slice plane $Z_r$.

Referring to 6(c), at slice plane position $Z_r$, the reconstruction of the voxels requires data be collected for approximately $2\pi$ of gantry rotation represented by projection line 70. For example, the voxels for a slice plane image at $Z_r$ for a given angle $\beta_1$ may be generally derived from the first, second, third, fourth, fifth and sixth detector elements 18 corresponding to z-axis locations $Z_1$, $Z_2$, $Z_3$, $Z_4$, $Z_5$, and $Z_6$, all within a column of detector array 44 at one gantry angle. For a preceding gantry of $\beta_2$, however, the helical movement of the gantry means that the z-axis locations of the detector elements 18' within the physical detector array 44, are no longer symmetrically clustered about the z-axis position of the slice plane $Z_r$. Accordingly, the same voxels may employ detector signals from the second, third, fourth, fifth and sixth detector elements 18' of a given column at the gantry angle $\beta_2$ and the detector signal from the first detector element of the same column at gantry position $\beta_2 + 2\pi$.

The operation of the selection of intensity signals during helical scanning results in the intensity signals from detector elements, at one end of the detector array 44, being dropped in favor of the intensity signals from detector elements with successive gantry angles $\beta + 2\pi$. The intent is to have the multiple z-axis positions of the intensity signals from the detector elements 18 to be close to the position of the slice plane $Z_r$.

Figure 6D:
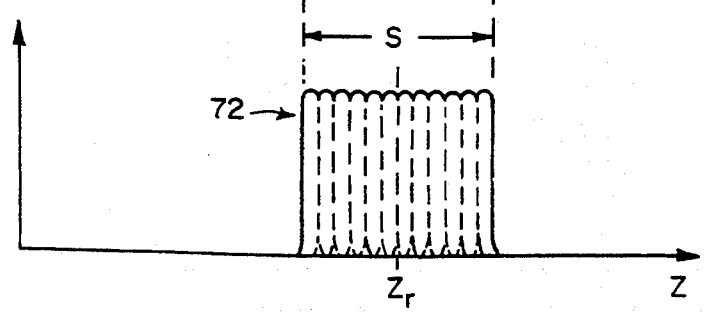
FIG. 6(d) is a graphical representation similar to FIG. 6(b) showing the effective slice profile of the fan beam of FIG. 6(a) after combining a number of single detector elements showing the improved slice profile obtained by the present invention.

When the voxels of the reconstructed signals from corresponding columns of each of the multiple rows are added together, the adding has the effect of broadening the effective slice profile s' of an individual detector element 18' to a composite slice profile 72 shown in FIG. 6(d). This composite slice profile 72 has a FWHM approximately equal to s and thus comports with the desired spatial resolution of the CT system and represents a clear advance over the slice profile provided by conventional CT helical scanning with interpolation.

Figure 7:
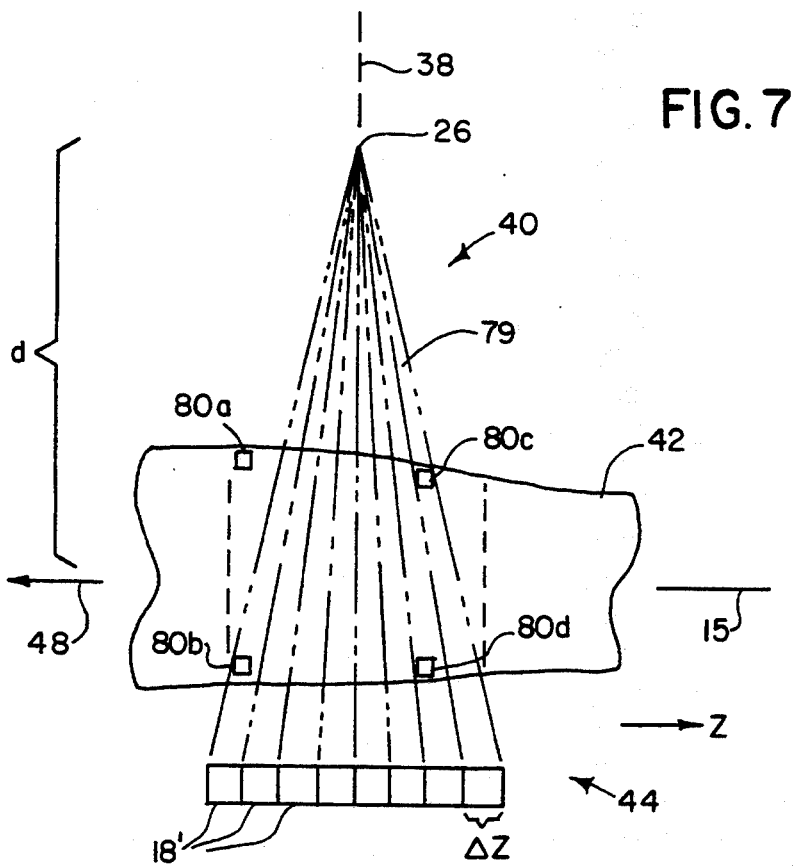
FIG. 7 is an exaggerated cross-section of the fan beam of FIG. 1, similar to FIG. 6(a), illustrating the source of reconstruction error resulting from the assumption of parallel rays in the reconstruction.

Referring now to FIG. 7, the present invention recognizes the fact that the fan beam 40 diverges slightly in the z-axis direction and therefore that rays 79 of the fan beam 40 as defined by the detector elements 18' are not parallel to each other nor to the gantry plane 38. While this divergence is small, it has an important effect in the reconstruction process which typically assumes that the rays 79 are parallel to the gantry plane 38.

When a conventional fan beam reconstruction technique is used, two voxels 80(c) and 80(d), in the patient 42, which lie in a plane parallel to the gantry plane 38, but intersect different rays 79 of the diverging fan beam 40, will be reconstructed as if they lie in different planes. As a result the reconstructed image will be distorted.

The divergence of the fan beam 40 also creates "partial volume effects" in that voxels 80(a) near the edge of the fan beam 40 will be intercepted by a ray 79 only for a portion of the gantry angles β during a rotation of the gantry in a complete circle and thus will contribute to some projections and not to others. Partial volume effects can create artifacts in the reconstructed image.

Figure 8A:
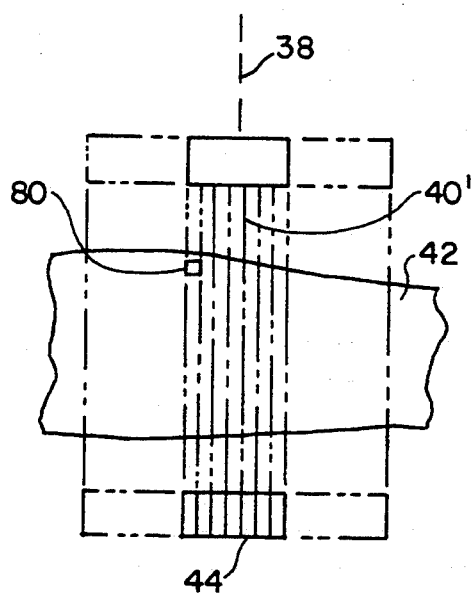
FIGS. 8(a) and 8(b) are exaggerated cross-sections of parallel and diverging fan beams showing the occurrence of twice-measured volumes of scanning for the diverging fan beam.
Figure 8B:
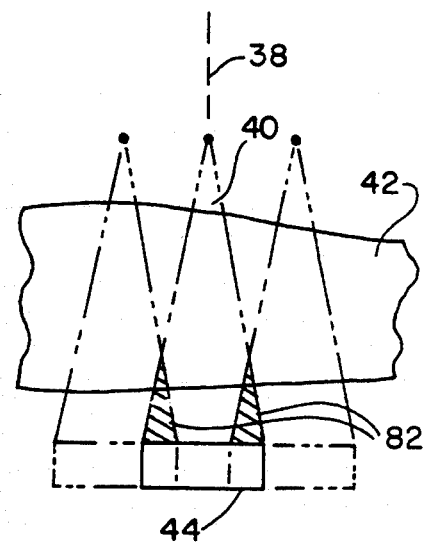

Referring to FIGS. 8(a) and 8(b), the divergence of the fan beam 40 about the gantry plane 38 also creates a problem of data that has been measured twice, a problem not present for truly parallel rays. In a parallel ray case shown in FIG. 8(a), for every $2\pi$ of gantry rotation, the detector array 44 may be advanced by its z-axis width to acquire projection data over a contiguous volume of the patient 42, i.e. so that each voxel 80 of the patient 42 is illuminated by one, and no more than one ray, at each gantry angle β. In contrast and as shown in FIG. 8(b), the divergence of the fan beam 40 along the z-axis causes it to cover less volume near the focal spot 26 than near the detector array 44. In order to obtain a complete projection set, that is, in order to have each voxel 80 illuminated by at least one ray for each angle β, the detector array 44 cannot be advanced by its full z-axis width but must be advanced a lesser amount depending on the exact divergence of the fan beam 40 from the gantry plane 38. This limitation on the amount of translation per gantry angle caused by the relative constriction of the fan beam near the source, creates some volumes 82 away from the source which have twice measured data, i.e., voxels 80 for which projection data has been acquired for two rays at a gantry angles separated by $2\pi$. This twice-measured data must be accounted for so as to not create artifacts in the reconstructed image.

Figure 9:
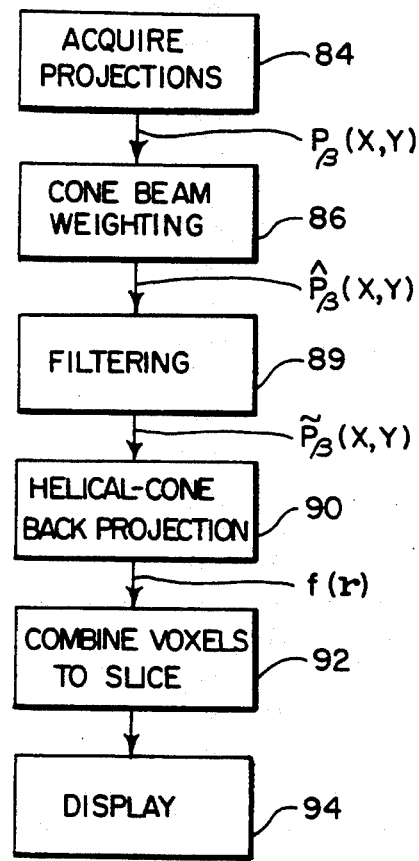
FIG. 9 is a flow chart illustrating the steps of reconstructing the data of the projections in the system of FIG. 3 according to the present invention.

Referring now to FIG. 9, these problems of the divergence of the fan beam 40 in the z-axis, as recognized by the present invention, may be remedied by applying a more sophisticated reconstruction method to the reconstruction of the projection data as allowed by the multi-row detector array 44. The reconstruction must accommodate the divergence of the fan beam 40 as well as the helical scanning of the present invention.

As shown by process block 84 of FIG. 9, the reconstruction process begins with the acquisition of projection data over a range of $2\pi$ of gantry angle or more. Each projection may be identified by its gantry β and by a y-axis and z-axis displacement relative to a center line of the fan beam 40 passing from the focal spot 26 perpendicular to the axis of rotation 15 of the gantry 20. Each of these projections may be represented by $P_\beta(Y,Z)$ for a planar detector 44 and $P_\beta(\gamma,Z)$ for a cylindrical detector 44.

The acquired projection data is next reconstructed not according to a fan beam reconstruction method but by employing a cone beam reconstruction method which takes into account the divergence of the fan beam 40. Cone beam reconstruction techniques are generally known for use in acquiring multiple slice images in a single rotation of the gantry. In the present invention, the cone beam technique is used with helical scanning. It is also used to reconstruct one slice image more accurately than can be done from an ordinary fan beam acquisition by making use of the data obtained from subdividing of the detector array into multiple rows of detectors. The relatively small divergence of the fan beam 40 in the z-axis radically improves the accuracy of the cone beam reconstruction which often is unsatisfactory for the larger cone beam angles.

The invention is applicable to any shape of detector and is described in detail for cylindrical detectors and planar detectors. The particular reconstruction technique employed in the preferred embodiment is based on that described in the paper "Practical Cone Beam Algorithm" by L. A. Feldkamp as reported in J. Opt. Soc. Am. A, Vol. 1, No. 6, June 1984, published by the Optical Society of America and incorporated into this specification by reference. This technique is modified to apply to curved detectors and to helical scanning.

1. Planar Detector Equations

For a planar detector, the reconstruction technique first weights each projection $P_{62}[Y,Z]$ as indicated by process block 86 to obtain a weighted projection $\hat{P}_\beta[Y, Z]$ as follows:

$$\hat{P}_\beta[Y, Z] = \frac{d}{\sqrt{d^2 + Y^2 + Z^2}} P_\beta[Y, Z] \tag{2}$$

where d is the distance between the focal spot 26 and the axis of rotation 15.

Next, as illustrated by process block 88, the weighted projections $\hat{P}_\beta[Y, Z]$ are filtered, according to their spatial frequency content in the y and z directions, to obtain a filtered projection $\check{P}_\beta[Y, Z]$ as follows:

$$\check{P}_\beta[Y, Z] = \tag{3}$$

$$\int_{-\infty}^{\infty} dY' \int_{-\infty}^{\infty} dZ' \hat{P}_\beta[Y', Z'] g_y(Y - Y') g_z(Z - Z')$$

where equation (3) will be recognized as a convolution effecting the filtering with convolution kernels $g_y(Y)$ and $g_z(Z)$. Such convolution is equivalent to multiplication in the frequency domain, as is well understood in the art, where filter kernels $g_y(Y)$ and $g_z(Z)$ are as follows:

$$g_y(Y) = \int_0^{\omega_y 0} d\omega \, \omega W(\omega) \cos(\omega Y) \tag{4}$$

where $W(\omega)$ is a window function as is known in the art.

Equation (4) is the Fourier transform of the standard tomographic filter which compensates for the proportionally greater amount of tomographic data that is obtained for low frequencies, by linearly de-weighting the lower frequency data. Equation (5) is the sinc function, or the Fourier transform of a rectangular low pass filter. $\omega_{y0}$ and $\omega_{z0}$ are the upper limits of the transmission band of the filters and may be $\pi/\Delta Z$ and $\pi/\Delta Y$ respectively, where $\Delta Z$ and $\Delta Y$ are the separation of the detector elements 18' in the z and y axis.

After weighting and filtering according to process blocks 86 and 89, a projection set of the projections are backprojected to voxels at process block 92.

The backprojection produces attenuation or density values f(r) for voxels of the image defined by vector notation where r is a vector designating the center of the voxel 80 and the backprojection follows the following equation:

$$f(r) = \frac{1}{4\pi^2} \oint d\beta \frac{d^2}{(d + r \cdot \hat{x}')^2} \tilde{P}_\beta[Y(r), Z(r)] \quad (6)$$

where:

f(r) is the density value of a reconstructed voxel defined by vector r.

Figure 10:
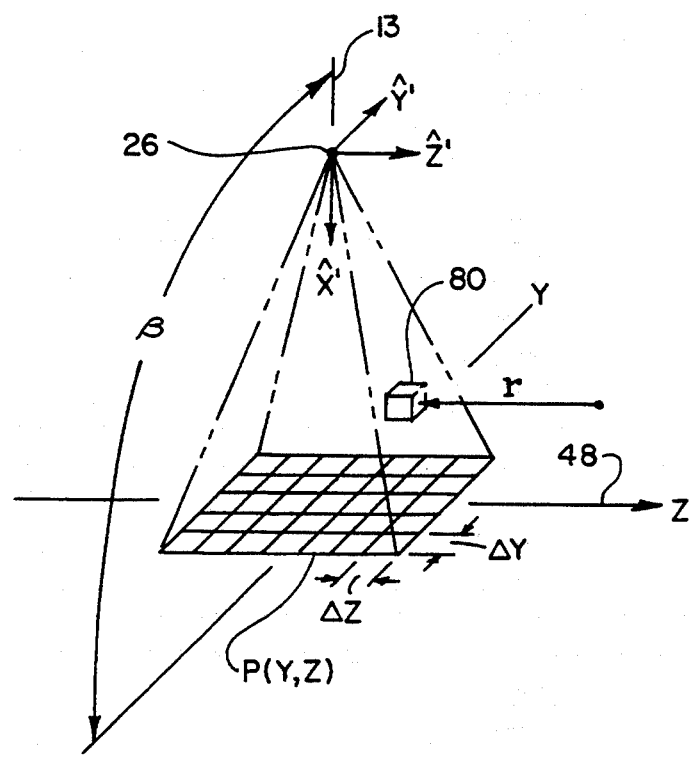
FIG. 10 is a diagram showing the rotating coordinates used for the reconstruction process of FIG. 9 for a planar detector.

The coordinates of the projection $\tilde{P}_\beta[Y(r), Z(r)]$ for the integration of equation (6) are determined for the cone beam as follows:

$$Y(r) = r \cdot \hat{y}' d/(d + r \cdot \hat{x}') \quad (7)$$

$$Z(r) = [r \cdot \hat{z}' - z_s(\beta)] d/(d + r \cdot \hat{x}') \quad (8)$$

where, referring to FIG. 10, $\hat{x}'$, $\hat{y}'$ and $\hat{z}'$ are unit vectors along the x', y' and z' axes, the former two which rotate with the movement of the gantry so that: x' is always aligned with the beam axis 13 of the fan beam 40, and y' is generally along the plane of the detector array 44, and the latter of which, z', is aligned with the axis of rotation 15. The term $z_s(\beta)$, provides the relative motion between the patient 42 and the focal spot 26 along the z axis and for a constant pitch helical scan as determined by the by the pitch s and is equal to $\beta/2\pi + z_0$ where H is the helical pitch which may equal but is not limited to s.

The backprojection of the projections $\tilde{P}_\beta[Y, Z]$ per equation (6) to density values f(r) for voxels 80, unlike a conventional fan beam backprojection, is along the actual path of the rays 79 as provided by equations (7) and (8) and hence takes into account the divergence of the rays 79 from the beam axis 13. A conventional fan beam system cannot employ a backprojection that takes into account the actual path of the rays 79 because the path information of the rays 79 is lost in their effective combination by the single row of detector elements 18 of the detector array 16 (shown in FIG. 1)

2. Cylindrical Detector Equations

Figure 11:
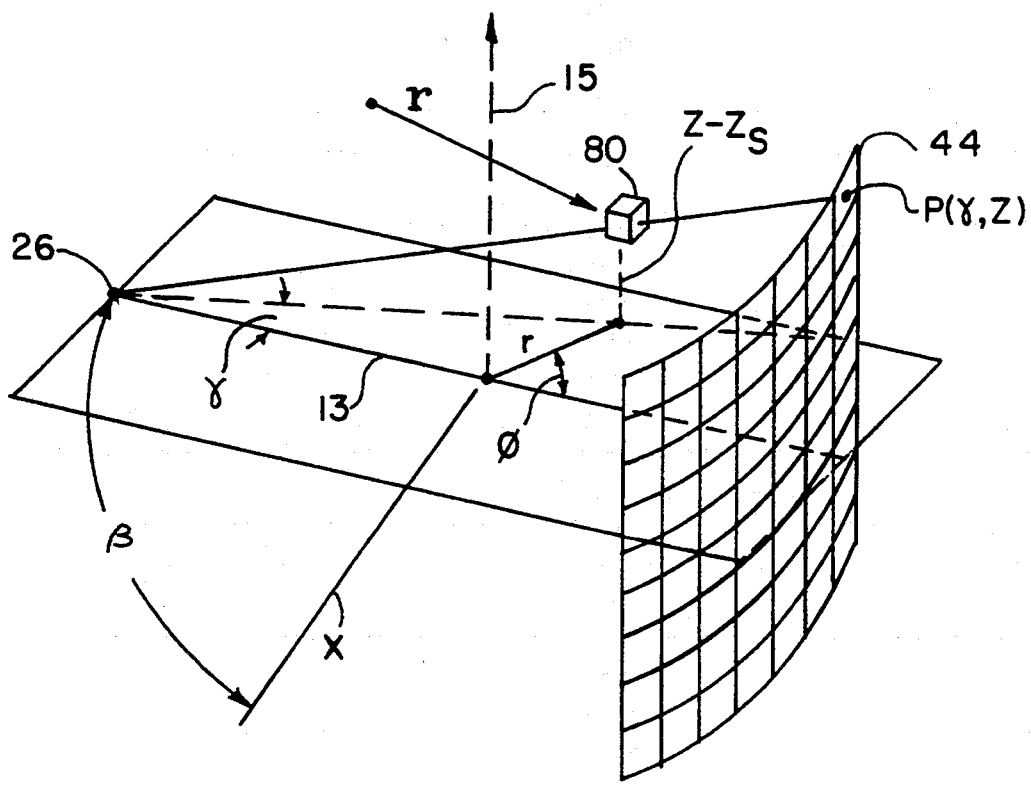
FIG. 11 is a diagram showing the coordinates used for the reconstruction process of FIG. 9 for a cylindrical detector.

Referring to FIG. 11, for a cylindrical detector array 44, the reconstruction technique first weights each projection $P_\beta[\gamma, Z]$ as indicated by process block 86 to obtain a weighted projection $\hat{P}_\beta[\gamma, Z]$ as follows:

$$\hat{P}_\beta[\gamma, Z] = \frac{Dd\cos(\gamma)}{\sqrt{d^2 + Z^2}} P_\beta[\gamma, Z] \quad (9)$$

where $\gamma$ is the angle within a plane parallel to the gantry plane between the focal spot 26 and the particular column of the detector element 18', D is the distance between the focal spot 26 and the axis of rotation 15 and d is the distance between the focal spot 26 and the detector element 18'.

Next, as illustrated again by process block 88, the weighted projections $\hat{P}_\beta[\gamma, Z]$ are filtered, according to their spatial frequency content in the $\gamma$ and z directions, to obtain a filtered projection $\tilde{P}_\beta[\gamma, Z]$ as follows:

$$\tilde{P}_\beta[\gamma, Z] = \int_{-\infty}^{\infty} d\gamma' \int_{-\infty}^{\infty} dZ' \hat{P}_\beta[\gamma', Z'] g_\gamma(\gamma - \gamma') g_z(Z - Z') \quad (10)$$

where equation (10) will be recognized as a convolution effecting the filtering with convolution kernels $g_\gamma(\gamma)$ and $g_z(Z)$. Such convolution is equivalent to multiplication in the frequency domain, as is well understood in the art, where filter kernels $g_\gamma(\gamma)$ and $g_z(Z)$ are as follows:

$$g_\gamma(\gamma) = \left(\frac{\gamma}{\sin(\gamma)}\right)^2 \int_0^{\omega_{\gamma 0}} d\omega \omega W(\omega) \cos(\omega Y) \quad (11)$$

where $W(\omega)$ is a window function as is known in the art.

Equation (11) is the Fourier transform of the standard tomographic filter which compensates for the proportionally greater amount of tomographic data that is obtained for low frequencies, by linearly de-weighting the lower frequency data. Equation (12) is the sinc function, or the Fourier transform of a rectangular low pass filter. $\omega_{\gamma 0}$ and $\omega_{z 0}$ are the upper limits of the transmission band of the filters and may be $\pi/\Delta Z$ and $\pi/\Delta \gamma$ respectively, where $\Delta Z$ and $\Delta \gamma$ are the separation of the detector elements 18' in the z and $\gamma$ axis.

After weighting and filtering according to process blocks 86 and 89, a projection set of the projections are backprojected to voxels at process block 92.

The backprojection produces attenuation or density values f(r) for voxels of the image defined by vector notation where r is a vector designating the center of the voxel 80 and the backprojection follows the following equation:

$$f(r) = \frac{1}{4\pi^2} \oint d\beta \frac{1}{E^2} \tilde{P}_\beta[\gamma(r), Z(r)] \quad (13)$$

where:

f(r) is the density value of a reconstructed voxel defined by vector r and $$E = \sqrt{D^2 + r^2 + 2rD\sin(\beta - \phi)} \quad (14)$$

where r and $\phi$ are polar coordinates of a point in the gantry plane measured about the center of rotation 15 and with respect to the x axis Which is fixed with respect to the patient 42.

The coordinates of the projection $\tilde{P}_\beta[\gamma(r), Z(r)]$ for the integration of equation (13) are determined for the cone beam as follows:

$$\gamma(r) = \tan^{-1} \frac{r\cos(\beta - \phi)}{D + r\sin(\beta - \phi)} \quad (15)$$

$$Z(r) = (z - z_s(\beta)) \frac{d}{E} \quad (16)$$

The term $z_s(\beta)$, provides the relative motion between the patient 42 and the focal spot 26 along the z axis and for a constant pitch helical scan as determined by the pitch H and is equal to $\beta/2\pi H + z_0$ where H is the helical pitch which may equal but is not limited to s.

As for the planar detector, the backprojection of the projections $P_\beta[\gamma, Z]$ per equation (13) to density values f(r) for voxels 80, unlike a conventional fan beam backprojection, is along the actual path of the rays 79 as provided by equations (15) and (16) and hence takes into account the divergence of the rays 79 from the beam axis 13. A conventional fan beam system cannot employ a backprojection that takes into account the actual path of the rays 79 because the path information of the rays 79 is lost in their effective combination by the single row of detector elements 18 of the detector array 16 (shown in FIG. 1)

At process block 92, the values f(r) of the reconstructed voxels 80 are summed to generate an image, the summing improving the signal-to-noise ratio of the resulting image. The voxels to be summed in the preferred embodiment are simply those flanking the desired slice plane $Z_r$ within a range of z values that may be equal to the total number of rows of detectors in the detector array 44. By summing the values f(r) of the voxels 80 rather than the intensity signals $P_\beta[X,Y]$ or $P_\beta[\gamma,Y]$ from each detector element 18', the divergence of the fan beam 40 from the beam axis 13 does not unnecessarily degrade the slice profile 72 as shown in FIG. 6(d).

The summing of the voxels 80 reflects the fact that the breaking of the detector array 44 into multiple rows of detector elements 18 is not intended to decrease the size of the slice thickness but to improve the slice profile. Summing of the voxels provides an image with similar z-axis resolution as would be provided in prior art CT systems under the stop and shoot methodology but permits the speed increases attendant to helical scanning without the adverse widening of the slice profile caused by interpolation.

Thus, the effect of the invention is to prevent the spreading of the effective slice profile and to reduce the artifacts associated with the fan beam's divergence along the z axis.

Many modifications and variations of the preferred embodiment which will still be within the spirit and scope of the invention will be apparent to those with ordinary skill in the art. Principally, the techniques of half scanning which recognizes an equivalence between projection acquired along rays 79 separated by only $\pi$ radians may be used with the above techniques allowing reconstruction of voxels from as little as $\pi$ gantry rotation. Different gantry angles where the columns of the detector 44 provide intensity signals along parallel rays will be termed "related angles". Further, although in the preferred embodiment, the detector elements are laid out in rectilinear rows and columns it will be recognized from the description of the invention, that the columns and rows need not be in straight lines so long as intensity signals along multiple rows may be measured. In order to apprise the public of the various embodiments that may fall within the scope of the invention, the following claims are made:

I claim:

1. A computed tomography apparatus producing images of an imaged object and comprising:
   an x-ray source directing an x-ray beam along a beam axis with movement of the beam axis throughout a plurality of beam angles about a translation axis, the beam including a plurality of rays along paths diverging conically from a focal spot and spaced apart in two dimensions with respect to the beam axis first along a translation axis in columns and second along a transverse axis perpendicular to the translation axis in rows;
   an array of detector elements receiving the x-ray beam after it passes through the imaged object, the elements arranged in columns along the translation axis and rows along the transverse axis, the rows and columns of the detector elements corresponding to the rows and columns of the rays, each detector element receiving a ray of the x-ray beam and producing an intensity signal dependant on the intensity of the ray of x-rays associated with that element, the intensity signals for the rows of detector elements forming a plurality of one dimensional row projections;
   a translator for moving the imaged object along the translation axis with respect to the x-ray source throughout a plurality of translation positions during the movement of the beam axis throughout the plurality of beam angles; and
   a filter for filtering the row projections of the projection set according to the spatial frequencies of the row projections;
   a backprojecting means for backprojecting each ray of a projection set of the row projections along the path of the ray to generate data for a volume of voxels, each voxel indicating the attenuation of the x-ray beam by a volume element of the imaged object;
   a combiner for combining selected voxels associated with rays near a predetermined slice plane into an image slice; and
   a display for displaying an image of the image slice.

2. The apparatus of claim 1, wherein the rows and columns of the detector elements are substantially within a single plane.

3. The apparatus of claim 2 wherein the backprojecting means operates according to the following formula:

$$f(r) = \frac{1}{4\pi^2} \oint d\beta \frac{d^2}{(d + r \cdot \hat{x}')^2} \tilde{P}_\beta[Y(r), Z(r)]$$

where:
f(r) is the attenuation of a given voxel defined by a spatial vector r;
d is the distance between the focal spot and the translation axis; $\hat{x}'$, $\hat{y}'$ and $\hat{z}'$ are orthogonal unit vectors oriented so that x' is always aligned with the beam axis and z', is aligned with the translation axis; and
where
$\tilde{P}_\beta[Y(r), Z(r)]$ is the filtered intensity signal of a row projection for a given beam angle $\beta$ associated with row Y and column Z, with $Y(r) = r \cdot \hat{y}' d/(d + r \cdot \hat{x}')$ $Z(r) = [r \cdot \hat{z}' - \hat{z}_s(\beta)] d/(d + r \cdot \hat{x}')$ and where $z_s(\beta)$ is a function providing the translation of the x-ray source to the change in beam angle; and further such that:

$$\tilde{P}_\beta[Y, Z] = \int_{-\infty}^{\infty} dY' \int_{-\infty}^{\infty} dZ' \hat{P}_\beta[Y', Z'] g_y(Y - Y') g_z(Z - Z')$$

with

-continued $$g_y(Y) = \int_0^{\omega_y 0} d\omega \omega W(\omega)\cos(\omega Y)$$

$g_z(Z) = \sin \omega_{z0} Z / \pi Z$ where $W(\omega)$ is a window function and $\hat{P}_\beta[Y, Z]$ is a weighted projection at row Y and column Z.

4. The apparatus of claim 1, wherein the rows and columns of the detector elements substantially conform to the surface of a cylinder.

5. The apparatus of claim 4 wherein the backprojecting means operates according to the following formula:

$$f(r) = \frac{1}{4\pi^2} \oint d\beta \frac{1}{E^2} \tilde{P}_\beta[\gamma(r), Z(r)]$$

where:
f(r) is the attenuation of a given voxel defined by a spatial vector r;
d is the distance between the focal spot and the translation axis;

$$E = \sqrt{D^2 + r^2 + 2rD\sin(\beta - \phi)}$$

where r and $\phi$ are polar coordinates of a point in a gantry plane measured about a center of rotation of the gantry and with respect to an x axis which is fixed with respect to the imaged object;
$\tilde{P}_\beta[\gamma(r), Z(r)]$ is the filtered intensity signal of a row projection for a given beam angle $\beta$ associated with row $\gamma$ and column Z
where:

$$\gamma(r) = \tan^{-1} \frac{r\cos(\beta - \phi)}{D + r\sin(\beta - \phi)}$$

$$Z(r) = (z - z_s(\beta)) \frac{d}{E}$$

and where, $z_s(\beta)$ is a function providing the translation of the x-ray source to the change in beam angle and further such that:

$$\tilde{P}_\beta[\gamma, Z] =$$

$$\int_{-\infty}^\infty d\gamma' \int_{-\infty}^\infty dZ' \hat{P}_\beta[\gamma', Z'] g_\gamma(\gamma - \gamma') g_z(Z - Z')$$

with $$g_\gamma(\gamma) = \left(\frac{\gamma}{\sin(\gamma)}\right)^2 \int_0^{\omega_y 0} d\omega \omega W(\omega)\cos(\omega Y)$$

$g_z(Z) = \sin \omega_{z0} Z / \pi Z$ where $W(\omega)$ is a window function and $\hat{P}_\beta[\gamma, Z]$ is a weighted projection at row $\gamma$ and column Z.

6. The apparatus of claim 1 wherein the beam angles associated with succeeding row projections are separated by an angular increment and wherein the projection set of row projection operated on by the backprojecting means includes only rays of row projections having beam angles in a range of not more than $2\pi$ minus the angular spacing centered on the voxel to be reconstructed.

7. The apparatus of claim 1 wherein the combiner takes the arithmetic sum of a predetermined number of voxels along the translation axis and centered about the predetermined slice plane.

8. The apparatus recited in claim 1 wherein the combiner sum a total number of voxels equal in extent along the translation axis to the desired spatial resolution of the image along the translation axis.

9. A method of generating images of an imaged object comprising the steps of:
generating an x-ray beam along a beam axis, the beam including a plurality of rays along paths diverging conically from a focal spot and spaced apart in two dimensions with respect to the beam axis first along a translation axis in columns and second along a transverse axis perpendicular to the translation axis in rows;
moving the beam axis throughout a plurality of beam angles about the translation axis;
receiving the x-ray beam after it passes through the imaged object at the plurality of beam angles for each ray to produce an intensity signal associated with each ray, the intensity signals for the row of rays forming a plurality of one dimensional row projections of a projection set;
translating the imaged object along the translation axis with respect to the x-ray source during the movement of the beam axis throughout the plurality of beam angles to obtain a projection set of row projections;
filtering the row projections of the projection set according to the spatial frequencies of the row projections;
backprojecting each ray of the projection set along the path of the ray to generate a volume of voxel data, each voxel indicating the attenuation of the x-ray beam by a volume element of the imaged object;
identifying a slice plane along the translation axis;
combining selected voxels associated with rays near the slice plane into an image slice; and
displaying an image of the image slice.

10. The method of claim 9 wherein the beam angles of succeeding row projections are separated by an angular spacing and wherein the step of backprojecting each ray of the projection set along its path backprojects only those rays of row projections having beam angles in a range of not more than $2\pi$ minus the angular spacing centered on the voxel to be reconstructed.

11. The method of claim 9 wherein the step of packprojection is according to the following formula:

$$f(r) = \frac{1}{4\pi^2} \oint d\beta \frac{d^2}{(d + r \cdot x')^2} \tilde{P}_\beta[Y(r), Z(r)]$$

where:
f(r) is the attenuation of a given voxel defined by a spatial vector r;
d is the distance between the focal spot and the translation axis;

$\hat{x}'$, $\hat{y}'$ and $\hat{z}'$ are orthogonal unit vectors oriented so that x' is always aligned with the beam axis and z', is aligned with the translation axis; and where $\tilde{P}_\beta[Y(r), Z(r)]$ is the filtered intensity signal of a row projection for a given beam angle $\beta$ associated with row Y and column Z, with $$Y(r) = r\hat{y}'d/(d + r\hat{x}')$$

$$Z(r) = [r\hat{z}' - z_s(\beta)]d/(d + r\hat{x}')$$

and where $z_s(\beta)$ is a function providing the translation of the x-ray source to the change in beam angle; and further such that:

$$\tilde{P}_\beta[Y, Z] = \int_{-\infty}^{\infty} dY' \int_{-\infty}^{\infty} dZ' \hat{P}_\beta[Y', Z'] g_Y(Y - Y') g_Z(Z - Z')$$

with $$g_Y(Y) = \int_0^{\omega_y 0} d\omega\, \omega\, W(\omega) \cos(\omega Y)$$

$g_Z(Z) = \sin \omega_{z0} Z / \pi Z$ where $W(\omega)$ is a window function and $\hat{P}_\beta[Y, Z]$ is a weighted projection at row Y and column Z.

12. The method of claim 9 wherein the step of backprojecting is according to the following formula:

$$f(r) = \frac{1}{4\pi^2} \oint d\beta \frac{1}{E^2} \tilde{P}_\beta[\gamma(r), Z(r)]$$

where:
f(r) is the attenuation of a given voxel defined by a spatial vector r;
d is the distance between the focal spot and the translation axis;

$$E = \sqrt{D^2 + r^2 + 2rD\sin(\beta - \phi)}$$

where r and $\phi$ are polar coordinates of a point in a gantry plane measured about a center of rotation of the gantry and with respect to an x axis which is fixed with respect to the imaged object;

$\tilde{P}_\beta[\gamma(r), Z(r)]$ is the filtered intensity signal of a row projection for a given beam angle $\beta$ associated with row $\gamma$ and column Z
where:

$$\gamma(r) = \tan^{-1} \frac{r\cos(\beta - \phi)}{D + r\sin(\beta - \phi)}$$

$$Z(r) = (z - z_s(\beta)) \frac{d}{E}$$

and where, $z_s(\beta)$ is a function providing the translation of the x-ray source to the change in beam angle and further such that:

$$\tilde{P}_\beta[\gamma, Z] = \int_{-\infty}^{\infty} d\gamma' \int_{-\infty}^{\infty} dZ' \hat{P}_\beta[\gamma', Z'] g_\gamma(\gamma - \gamma') g_Z(Z - Z')$$

with $$g_\gamma(\gamma) = \left(\frac{\gamma}{\sin(\gamma)}\right)^2 \int_0^{\omega_y 0} d\omega\, \omega\, W(\omega) \cos(\omega Y)$$

$g_Z(Z) = \sin \omega_{z0} Z / \pi Z$ where $W(\omega)$ is a window function and $\tilde{P}_\beta[\gamma, Z]$ is a weighted projection at row $\gamma$ and column Z.

13. The method of claim 9 wherein the step of combining the selected voxels into image slices takes the arithmetic sum of a predetermined number of voxels along the translation axis and centered about a predetermined slice plane.

14. The method recited in claim 9 wherein the step of combining the selected voxels into image slices sums a total number of voxels equal in extent along the translation axis to the desired spatial resolution of the image along the translation axis.

* * * * *

UNITED STATES PATENT AND TRADEMARK OFFICE
CERTIFICATE OF CORRECTION

PATENT NO. : 5,377,250

DATED : December 27, 1994

INVENTOR(S) : Hui Hu

It is certified that error appears in the above-identified patent and that said Letters Patent is hereby corrected as shown below:

Col. 4, line 59  "as shogun" should be --as shown--

Col. 8, line 62  "con, hands" should be --commands--

Col. 9, line 34  "28' shogun" should be --28' shown in--

Col. 12, line 29  "$P_{62}$" should be --$P\beta$--

Col. 12, lines 42,44  "$\hat{P}_\beta$" should be $\tilde{P}_\beta$

Col. 12, line 59  $$g_z(Z) = \sin \omega_{z0} Z / \pi Z \qquad (5)$$

Col. 13, line 13

$$"f(\mathbf{r}) = \frac{1}{4\pi^2} \oint d\beta \frac{d^2}{(d + \mathbf{r}\cdot\mathbf{x}')^2} \beta[Y(\mathbf{r}), Z(\mathbf{r})] \quad (6)"$$

should be $$f(\mathbf{r}) = \frac{1}{4\pi^2} \oint d\beta \frac{d^2}{(d + \mathbf{r}\cdot\hat{\mathbf{x}}')^2} P_\beta[Y(\mathbf{r}), Z(\mathbf{r})] \quad (6)$$

UNITED STATES PATENT AND TRADEMARK OFFICE
CERTIFICATE OF CORRECTION

PATENT NO. : 5,377,250

DATED : December 27, 1994

INVENTOR(S) : Hui Hu

It is certified that error appears in the above-identified patent and that said Letters Patent is hereby corrected as shown below:

| | |
|---|---|
| Col. 13, line 38 | "pitch S" should be --pitch H-- |
| Col. 13 lines 39 | "$\beta/2\pi$" should be --$\frac{\beta}{2\pi}H$-- |
| Col. 14, line 67 | "$\beta/2\pi$" should be --$\frac{\beta}{2\pi}H$-- |
| Col. 14, line 18 | insert --$g_z(Z) = \sin\omega_{z0}Z/\pi Z$  (12)-- |
| Col. 14, line 52 | "axis Which" should be --axis which-- |
| Col. 15, line 2 | "$P_\beta[\gamma, Z]$" should be --$\tilde{P}_\beta[\gamma, Z]$-- |

UNITED STATES PATENT AND TRADEMARK OFFICE
CERTIFICATE OF CORRECTION

PATENT NO. : 5,377,250

DATED : December 27, 1994

INVENTOR(S) : Hui Hu

It is certified that error appears in the above-identified patent and that said Letters Patent is hereby corrected as shown below:

Columns 16, 17, 18, 19, & 20
Claims 3, 5, 11 and 12
should read as follows:

3. The apparatus of claim 2 wherein the backprojecting means operates according to the following formula:

$$f(r) = \frac{1}{4\pi^2} \oint d\beta \frac{d^2}{(d + r \cdot \hat{x}')^2} \tilde{P}_\beta[Y(r), Z(r)]$$

where:

$f(r)$ is the attenuation of a given voxel defined by a spatial vector r;

d is the distance between the focal spot and the translation axis;

$\hat{x}'$, $\hat{y}'$ and $\hat{z}'$ are orthogonal unit vectors oriented so that x' is always aligned with the beam axis and z', is aligned with the translation axis; and where

UNITED STATES PATENT AND TRADEMARK OFFICE
CERTIFICATE OF CORRECTION

PATENT NO. : 5,377,250
DATED : December 27, 1994
INVENTOR(S) : Hui Hu It is certified that error appears in the above-identified patent and that said Letters Patent is hereby corrected as shown below:

$\tilde{P}_\beta[Y(r), Z(r)]$ is the filtered intensity signal of a row projection for a given beam angle $\beta$ associated with row 15  Y and column Z, with $Y(r) = r \cdot \hat{y}' d/(d + r \cdot \hat{x}')$ $Z(r) = [r \cdot \hat{z}' - z_s(\beta)]d/(d + r \cdot \hat{x}')$ and where $z_s(\beta)$ is a function providing the translation of the x-ray source to the change in beam angle; and further 20  such that:

$$\tilde{P}_\beta[Y, Z] = \int_{-\infty}^{\infty} dY' \int_{-\infty}^{\infty} dZ' \, \hat{P}_\beta[Y', Z'] g_y(Y - Y') \, g_z(Z - Z')$$

with $$g_y(Y) = \int_{0}^{\omega_{y0}} d\omega \, \omega W(\omega) \cos(\omega Y)$$

$$g_z(Z) = \sin \omega_{z0} Z / \pi Z$$

UNITED STATES PATENT AND TRADEMARK OFFICE
CERTIFICATE OF CORRECTION

PATENT NO. : 5,377,250
DATED : December 27, 1994
INVENTOR(S) : Hui Hu It is certified that error appears in the above-identified patent and that said Letters Patent is hereby corrected as shown below:

where $W(\omega)$ is a window function and $\hat{P}_\beta[Y, Z]$ is a weighted projection at row Y and column Z.

5. The apparatus of claim 4 wherein the backprojecting means operates according to the following formula:

$$f(r) = \frac{1}{4\pi^2} \oint d\beta \frac{1}{E^2} \tilde{P}_\beta[\gamma(r), Z(r)]$$

where:

$f(r)$ is the attenuation of a given voxel defined by a spatial vector r;

d is the distance between the focal spot and the translation axis;

$$E = \sqrt{D^2 + r^2 + 2rD\sin(\beta-\phi)}$$

where r and $\phi$ are polar coordinates of a point in a gantry plane measured about a center of rotation of the gantry and with respect to an x axis which is fixed with respect to the imaged object;

UNITED STATES PATENT AND TRADEMARK OFFICE
CERTIFICATE OF CORRECTION

PATENT NO. : 5,377,250

DATED : December 27, 1994

INVENTOR(S) : Hui Hu

It is certified that error appears in the above-identified patent and that said Letters Patent is hereby corrected as shown below:

15      $\tilde{P}_\beta[\gamma(r), Z(r)]$ is the filtered intensity signal of a row projection for a given beam angle $\beta$ associated with row $\gamma$ and column $Z$ where:

$$\gamma(r) = \tan^{-1} \frac{r\cos(\beta-\phi)}{D+r\sin(\beta-\phi)}$$

20      $$Z(r) = (z-z_S(\beta))\frac{d}{E}$$

and where, $z_S(\beta)$ is a function providing the translation of the x-ray source to the change in beam angle and further such that:

$$\tilde{P}_\beta[\gamma, Z] = \int_{-\infty}^{\infty} d\gamma' \int_{-\infty}^{\infty} dZ' \; \hat{P}_\beta[\gamma', Z'] g_\gamma(\gamma - \gamma') \; g_z(Z - Z')$$

25      with $$g_\gamma(\gamma) = \left[\frac{\gamma}{\sin(\gamma)}\right]^2 \int_0^{\omega_{y0}} d\omega \, \omega W(\omega)\cos(\omega Y)$$

$$g_z(Z) = \sin \omega_{z0} Z/\pi Z$$

UNITED STATES PATENT AND TRADEMARK OFFICE
CERTIFICATE OF CORRECTION

PATENT NO. : 5,377,250
DATED : December 27, 1994
INVENTOR(S) : Hui Hu It is certified that error appears in the above-identified patent and that said Letters Patent is hereby corrected as shown below:

where $W(\omega)$ is a window function and $\hat{P}_\beta[\gamma, Z]$ is a weighted projection at row $\gamma$ and column $Z$.

11. The method of claim 9 wherein the [setop] *Step* of packprojection is according to the following formula:

$$f(\mathbf{r}) = \frac{1}{4\pi^2} \oint d\beta \, \frac{d^2}{(d + \mathbf{r}\cdot\hat{x}')^2} \, \tilde{P}_\beta[Y(\mathbf{r}), Z(\mathbf{r})]$$

where:

$f(\mathbf{r})$ is the attenuation of a given voxel defined by a spatial vector $\mathbf{r}$;

$d$ is the distance between the focal spot and the translation axis;

$\hat{x}'$, $\hat{y}'$ and $\hat{z}'$ are orthogonal unit vectors oriented so that $x'$ is always aligned with the beam axis and $z'$, is aligned with the translation axis; and where $\tilde{P}_\beta[Y(\mathbf{r}), Z(\mathbf{r})]$ is the filtered intensity signal of a row projection for a given beam angle $\beta$ associated with row

UNITED STATES PATENT AND TRADEMARK OFFICE
CERTIFICATE OF CORRECTION

PATENT NO. : 5,377,250
DATED : December 27, 1994
INVENTOR(S) : Hui Hu It is certified that error appears in the above-identified patent and that said Letters Patent is hereby corrected as shown below:

Y and column Z, with $Y(r) = r \cdot \hat{y}' d/(d + r \cdot \hat{x}')$ $Z(r) = [r \cdot \hat{z}' - z_s(\beta)]d/(d + r \cdot \hat{x}')$ and where $z_s(\beta)$ is a function providing the translation of the x-ray source to the change in beam angle; and further such that:

$$\tilde{P}_\beta[Y, Z] = \int_{-\infty}^{\infty} dY' \int_{-\infty}^{\infty} dZ' \, \hat{P}_\beta[Y', Z'] g_y(Y - Y') \, g_z(Z - Z')$$

with $$g_y(Y) = \int_0^{\omega_{y0}} d\omega \, \omega W(\omega) \cos(\omega Y)$$

$$g_z(Z) = \sin \omega_{z0} Z / \pi Z$$

where $W(\omega)$ is a window function and $\hat{P}_\beta[Y, Z]$ is a weighted projection at row Y and column Z.

UNITED STATES PATENT AND TRADEMARK OFFICE
CERTIFICATE OF CORRECTION

PATENT NO. : 5,377,250
DATED : December 27, 1994
INVENTOR(S) : Hui Hu

It is certified that error appears in the above-identified patent and that said Letters Patent is hereby corrected as shown below:

12. The method of claim 9 wherein the step of backprojecting is according to the following formula:

$$f(r) = \frac{1}{4\pi^2} \oint d\beta \frac{1}{E^2} \tilde{P}_\beta[\gamma(r), Z(r)]$$

where:

5     $f(r)$ is the attenuation of a given voxel defined by a spatial vector r;

d is the distance between the focal spot and the translation axis;

$$E = \sqrt{D^2 + r^2 + 2rD\sin(\beta-\phi)}$$

10     where r and $\phi$ are polar coordinates of a point in a gantry plane measured about a center of rotation of the gantry and with respect to an x axis which is fixed with respect to the imaged object;

$\tilde{P}_\beta[\gamma(r), Z(r)]$ is the filtered intensity signal of a 15     row projection for a given beam angle $\beta$ associated with row $\gamma$ and column Z

UNITED STATES PATENT AND TRADEMARK OFFICE
CERTIFICATE OF CORRECTION

PATENT NO. : 5,377,520
DATED : December 27, 1994
INVENTOR(S) : Hui Hu

It is certified that error appears in the above-indentified patent and that said Letters Patent is hereby corrected as shown below:

where:

$$\gamma(r) = \tan^{-1} \frac{r\cos(\beta-\phi)}{D+r\sin(\beta-\phi)}$$

$$Z(r) = (z-z_S(\beta))\frac{d}{E}$$

and where, $z_S(\beta)$ is a function providing the translation of the x-ray source to the change in beam angle and further such that:

$$\tilde{P}_\beta[\gamma, z] = \int_{-\infty}^{\infty} d\gamma' \int_{-\infty}^{\infty} dz' \hat{P}_\beta[\gamma', z'] g_\gamma(\gamma - \gamma') g_z(z - z')$$

with

UNITED STATES PATENT AND TRADEMARK OFFICE
CERTIFICATE OF CORRECTION

PATENT NO. : 5,377,520
DATED : December 27, 1994
INVENTOR(S) : Hui Hu

It is certified that error appears in the above-indentified patent and that said Letters Patent is hereby corrected as shown below:

$$25 \quad g_\gamma(\gamma) = \left[\frac{\gamma}{\sin(\gamma)}\right]^2 \int_0^{\omega y0} d\omega\, \omega W(\omega)\cos(\omega Y)$$

$$g_Z(Z) = \sin \omega_{z0} Z / \pi Z$$

where $W(\omega)$ is a window function and $\hat{P}_\beta[\gamma, Z]$ is a weighted projection at row $\gamma$ and column Z.

Signed and Sealed this

Twenty-fifth Day of April, 1995

Attest:

BRUCE LEHMAN

Attesting Officer    Commissioner of Patents and Trademarks